US012605060B1

(12) United States Patent
Ho et al.

(10) Patent No.: US 12,605,060 B1
(45) Date of Patent: Apr. 21, 2026

(54) BALLOON DEVICE FOR RIGID BRONCHOSCOPY

(71) Applicants: An Ho, Glendale, AZ (US); David Stein, Queens Creek, AZ (US)

(72) Inventors: An Ho, Glendale, AZ (US); David Stein, Queens Creek, AZ (US)

( * ) Notice: Subject to any disclaimer, the term of this patent is extended or adjusted under 35 U.S.C. 154(b) by 0 days.

(21) Appl. No.: 18/923,845

(22) Filed: Oct. 23, 2024

(51) Int. Cl.
| | |
|---|---|
| *A61B 1/00* | (2006.01) |
| *A61B 1/267* | (2006.01) |
| *A61M 25/10* | (2013.01) |

(52) U.S. Cl.
CPC ........ *A61B 1/2676* (2013.01); *A61B 1/00082* (2013.01); *A61M 25/10184* (2013.11)

(58) Field of Classification Search
CPC .............. A61B 1/00082; A61B 1/2676; A61B 1/00135; A61B 1/00137; A61B 1/0014; A61M 25/10184
See application file for complete search history.

(56) References Cited

U.S. PATENT DOCUMENTS

| | | | | | |
|---|---|---|---|---|---|
| 4,886,496 | A | | 12/1989 | Conoscenti et al. | |
| 5,056,529 | A | * | 10/1991 | de Groot | A61B 10/04 600/569 |
| 5,374,261 | A | * | 12/1994 | Yoon | A61B 17/12022 604/11 |
| 2010/0163023 | A1 | * | 7/2010 | Singh | A61M 16/044 73/1.01 |
| 2012/0178994 | A1 | * | 7/2012 | Schembre | A61B 1/31 600/115 |
| 2014/0088457 | A1 | | 3/2014 | Johnson | |
| 2014/0316207 | A1 | * | 10/2014 | Hain | A61B 1/00073 600/194 |
| 2016/0038008 | A1 | * | 2/2016 | Molnar | A61B 1/00137 600/110 |
| 2019/0314620 | A1 | * | 10/2019 | Chang | A61B 5/6852 |
| 2022/0095901 | A1 | * | 3/2022 | Flanagan | A61B 1/018 |
| 2025/0073412 | A1 | * | 3/2025 | Burke | A61B 1/00154 |

* cited by examiner

*Primary Examiner* — Timothy J Neal
(74) *Attorney, Agent, or Firm* — Ziegler IP Law Group, LLC.

(57) ABSTRACT

A balloon device for a rigid bronchoscope includes a balloon shaft member; a balloon member connected to the balloon shaft member; and an inflation device operably connected to the balloon shaft member and the balloon member. The inflation device configured to adjust an inflation level of the balloon member. The inflatable and adjustable balloon device is configured to fit snugly on the outside of the rigid bronchoscope. This enables better ventilation of patient's undergoing rigid bronchoscopy and prevents back bleeding into the lung. Once the balloon is inflated, improved jet ventilation can occur with better resulting aeration.

7 Claims, 9 Drawing Sheets

812

BALLOON DEVICE FOR RIGID BRONCHOSCOPY

TECHNICAL FIELD

The aspects of the disclosed embodiments relate generally to rigid bronchoscopy and more particularly to a rigid bronchoscopy balloon device.

BACKGROUND

Rigid bronchoscopy is a medical procedure used to examine and treat the inside of the airways. It is a commonly performed procedure among interventional pulmonologists. Indications for rigid bronchoscopy include relief of airway obstructions, dilation of airways structures, control of airway bleeding, tissue biopsies and insertion of airway stents. During this procedure the airway is shared between the pulmonologist and the anaesthesiologist to ensure adequate ventilation.

Rigid bronchoscopes come in varied sizes with a uniform overall construction. They consist of a solid metal tube which is open at both ends with side holes along the distal aspect of the scope, which is used for ventilation, most commonly jet (Venturi) ventilation. The other proximal components consist of the illumination channel as well as the working channel.

A common dilemma encountered during rigid bronchoscopy is the lack of consistent ventilation. Frequently, large leaks are observed and can preclude adequate ventilation. The high pressures during jet ventilation can leak up through the proximal upper airway which requires oral pharyngeal or nasal packing to prevent large airway leaks. Also, decreased chest wall compliance as seen in patients with pulmonary pathology or in patients who are morbidly obese can aggravate proper ventilation. An additional problem encountered during rigid bronchoscopy is back bleeding, up and around the scope, to the side which is being ventilated Thus, there is a need for and improved rigid bronchoscope. Accordingly, it would be desirable to provide an apparatus or device that addresses at least some of the problems described above.

SUMMARY

The aspects of the disclosed embodiments are directed to a balloon device for a rigid bronchoscope. The balloon device of the disclosed embodiments is inflatable and adjustable and configured to enable better ventilation of a patient undergoing a rigid bronchoscopy and prevent bleeding into the ventilated lung.

According to a first aspect, the above and further advantages are obtained by a balloon device for a rigid bronchoscope. In one embodiment, the balloon device includes a balloon shaft member; a balloon member connected to the balloon shaft member; and an inflation device operably connected to the balloon shaft member and the balloon member. The inflation device is configured to adjust an inflation level of the balloon member.

In a possible implementation form, the balloon member comprises a circular balloon member disposed between a first circular edge member and a second circular edge member, wherein a dimension of the circular balloon member between the first circular edge member and the second circular edge member is a constant and a diameter of the first circular edge member and the second circular edge member is configured to vary.

In a possible implementation form the first circular edge member and the second circular edge member comprise rubber band members.

In a possible implementation form a rigid circular tube member is connected to the balloon shaft member. The balloon member is disposed over the rigid circular tube member and configured to configured to expand radially outward from the rigid circular tube member when inflated.

In a possible implementation form the rigid circular tube member further comprises fenestrated holes that are configured to allow air to pass to and from the balloon shaft member and the balloon member.

In a possible implementation form a diameter of the rigid circular tube member is fixed.

In a possible implementation form a diameter of the balloon member around the rigid circular tube member varies based on the inflation level of the balloon member.

In a possible implementation form a metal string member is connected to an end of the balloon shaft member and the balloon member is connected to the metal string member.

In a possible implementation form the metal string member has a circular shape and a diameter of the circular shape is adjustable.

In a possible implementation form a diameter of the balloon member varies with a change in the diameter of the circular shape of the metal string member.

In a possible implementation form the balloon shaft member is connected between an air installation port and the balloon member and is configured to deliver air from the air installation port to the balloon member.

In a possible implementation form the balloon member comprises a biocompatible material.

According to a second aspect, the above and further advantages are obtained by a rigid bronchoscope. In one embodiment, the rigid bronchoscope includes a barrel member; and a ballon device disposed on the barrel member. The balloon device has a balloon shaft member; a balloon member connected to the balloon shaft member and an inflation device operably connected to the balloon shaft member and the balloon member. The inflation device is configured to adjust an inflation level of the balloon member to cause the balloon member to seal around the barrel of the rigid bronchoscope.

In a possible implementation form the balloon member comprises a circular balloon member disposed between a first circular edge member and a second circular edge member, wherein a dimension of the circular balloon member between the first circular edge member and the second circular edge member is a constant and a diameter of the first circular edge member and the second circular edge member is configured to vary to accommodate a diameter of the barrel member.

In a possible implementation form a rigid circular tube member is connected to the balloon shaft member. The balloon member is disposed over the rigid circular tube member and configured to configured to expand radially outward from the rigid circular tube member to seal at least against the barrel member when inflated.

In a possible implementation form the rigid circular tube member further comprises fenestrated holes that are configured to allow air to pass to and from the balloon shaft member and the balloon member.

In a possible implementation form a metal string member is connected to an end of the balloon shaft member and the balloon member is connected to the metal string member.

In a possible implementation form the metal string member has a circular shape and a diameter of the circular shape is adjustable to conform to a diameter of the barrel member.

In a possible implementation form a diameter of the balloon member varies with a change in the diameter of the circular shape of the metal string member.

In a possible implementation form movement of the ballon shaft member is configured to move the balloon member over the barrel member.

According to a third aspect, the above and further advantages are obtained by a rigid bronchoscope. In one embodiment, the rigid bronchoscope includes a rigid tubular body configured for insertion into a patient's airway; an inflatable balloon positioned on the exterior surface of the rigid tubular body; and an inflation mechanism operably connected to the inflatable balloon. The inflation mechanism is configured to adjust the inflation level of the balloon.

In a possible implementation form, the balloon is configured to provide a seal within the airway to prevent the egress of air from the lung during procedures.

In a possible implementation form, the inflatable balloon is made of a biocompatible material.

In a possible implementation form, a control unit is operably connected to the inflation mechanism, the control unit configured to provide precise control over the inflation and deflation of the balloon.

In a possible implementation form, the control unit includes a manual control interface allowing for manual adjustment of the balloon inflation level.

In a possible implementation form, the control unit includes an automatic control system configured to maintain a predetermined inflation level based on feedback from sensors or a pilot balloon positioned on or near the inflatable balloon.

In a possible implementation form, the inflatable balloon is segmented into multiple independently inflatable sections, each section operably connected to the inflation mechanism.

In a possible implementation form, the control unit is configured to independently control the inflation level of each segmented section of the inflatable balloon.

In a possible implementation form, the inflation mechanism comprises a pump and a valve system to regulate the flow of inflation fluid into and out of the balloon.

In a possible implementation form, the inflation fluid is a gas selected from the group consisting of air, oxygen, and carbon dioxide.

In a possible implementation form, the inflatable balloon is positioned near the distal end of the rigid tubular body.

In a possible implementation form, the balloon device further includes a visual indicator on the rigid tubular body to indicate the inflation level of the balloon.

In a possible implementation form, the inflatable balloon is configured to expand radially outward from the rigid tubular body.

In a possible implementation form, the inflatable balloon is detachable from the rigid tubular body for replacement or sterilization.

In a possible implementation form, the inflatable balloon is fixated on a circular plastic tube.

In a possible implementation form, the circular tube has a fixed diameter.

In a possible implementation form, the circular tube has fenestrated holes that are used to inflate the balloon via the connecting tube.

In a possible implementation form a circular metal strip or string is connected to an end of the connecting tubing.

In a possible implementation form, a diameter of the circular metal strip is adjustable.

In a possible implementation form, a balloon member is attached to an outer perimeter of the circular metal strip.

These and other aspects, implementation forms, and advantages of the exemplary embodiments will become apparent from the embodiments described herein considered in conjunction with the accompanying drawings. It is to be understood, however, that the description and drawings are designed solely for purposes of illustration and not as a definition of the limits of the disclosed invention, for which reference should be made to the appended claims. Additional aspects and advantages of the invention will be set forth in the description that follows, and in part will be obvious from the description, or may be learned by practice of the invention. Moreover, the aspects and advantages of the invention may be realized and obtained by means of the instrumentalities and combinations particularly pointed out in the appended claims.

BRIEF DESCRIPTION OF THE DRAWINGS

In the following detailed portion of the present disclosure, the invention will be explained in more detail with reference to the example embodiments shown in the drawings, in which like references indicate like elements and.

DETAILED DESCRIPTION OF THE DISCLOSED EMBODIMENTS

Figure 1:
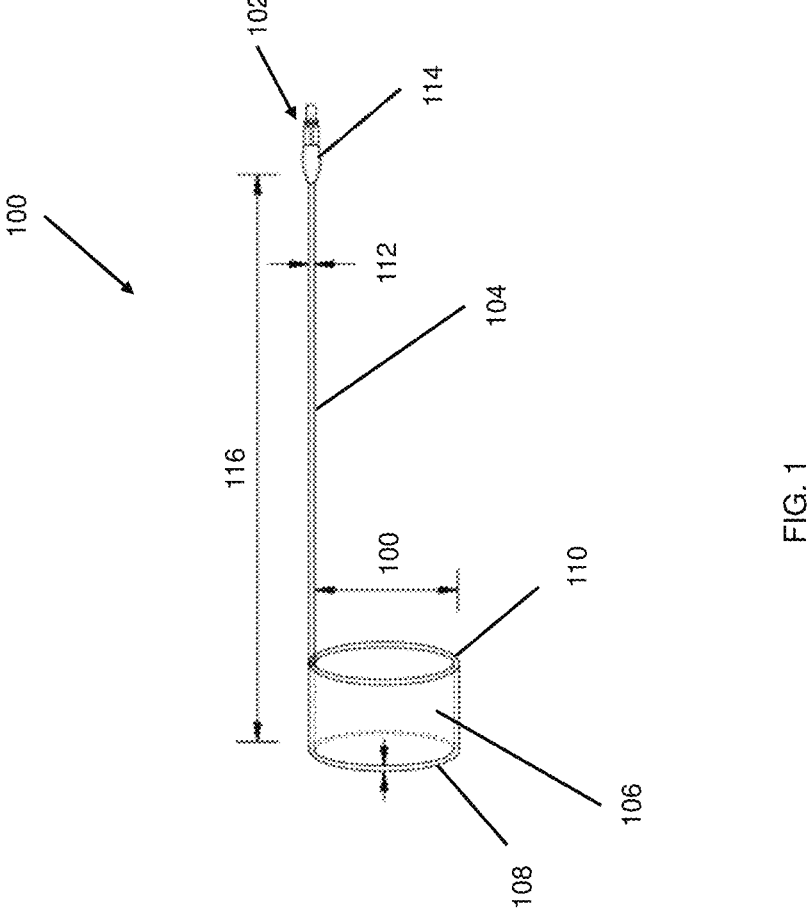
FIG. 1 illustrates a schematic block diagram of an exemplary ballon device for a rigid bronchoscope incorporating aspects of the disclosed embodiments.

FIG. 1 illustrates a schematic block diagram of an exemplary balloon device 100 for a rigid bronchoscope incorporating aspects of the disclosed embodiments. The aspects of the disclosed embodiments are directed to an adjustable and inflatable balloon device for a rigid bronchoscope device. The balloon device 100 is configured to fit on an outside of the barrel of the rigid bronchoscope.

Once the balloon is inflated improved jet ventilation can occur with better resulting aeration secondary to reduced air leakage. The better airway seal the balloon device 100 of the disclosed embodiments allows for more directed control of ventilation and enhanced measurements of end tidal carbon dioxide (ETCO2), which is difficult to accurately obtain during jet ventilation.

The balloon device 100 of the disclosed embodiments can be used to enter the main airway of a bleeding lung. Once inflated, bleeding can be contained to the pathological lung and spare the healthy, ventilated lung.

As illustrated in the example of FIG. 1, the balloon device 100 of the disclosed embodiments has two main parts, an air installation port 102 and a main balloon member 106. A balloon shaft or connecting tube 104 is coupled between the air installation port 102 and the main balloon member 106.

The air installation port 102 is generally a one-way valve that allows air to be delivered through the air installation port 102 to the main balloon member 106. In one embodiment, the air installation port 102 can include a pilot balloon 114. An inflated pilot balloon 114 can indicate an inflated main balloon member 106.

The balloon shaft 104 is generally configured to provide air to the balloon member 106 for inflation when air is delivered to or through the air installation port 102. In one embodiment, the balloon shaft 104 is a hollow tube that connects to and between the main balloon member 106 and the air installation port 102.

A diameter 112 of the balloon shaft 104 can be approximately 1 millimeter. In alternate embodiments, the diameter 112 of the balloon shaft can be of any suitable size, other than including 1 mm. A length 116 of the balloon shaft 106 can be approximately 30 centimeters (cm). In alternate embodiments, the length 116 of the balloon shaft 104 can be any suitable length other than including 30 cm.

In one embodiment, the main balloon member 106 is a tube-like rubber band with two outer edges 108, 110. The main balloon member 106 can be made of latex or polyurethane. In alternate embodiments, the material of the main balloon member 106 can be any suitable material that has high compatibility and inflatability. The material should be soft, not too hard on the airway of the patient, and still provide a good seal.

Figure 2:
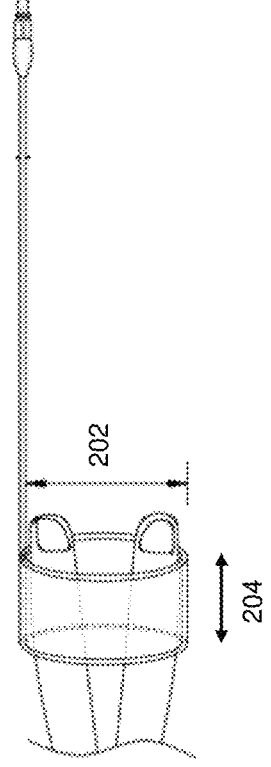
FIG. 2 illustrates the stretchability of the balloon device shown in FIG. 1.

FIG. 2 illustrates the stretchability of the main balloon member 106. In one embodiment, a distance 204 between the first edge 108 and the second edge 110 is fixed. The diameter 202 is configured to vary to accommodate different sizes of the barrel 302 of a rigid bronchoscope 300.

As will be described below with respect to FIG. 3, the main balloon member 106 is configured to fit over the barrel 302 of a rigid bronchoscope 300. The fit should be snug, or tight enough to hold securely against the barrel 302, creating a seal to prevent movement, leakage, or the passage of fluids or gases.

Figure 3:
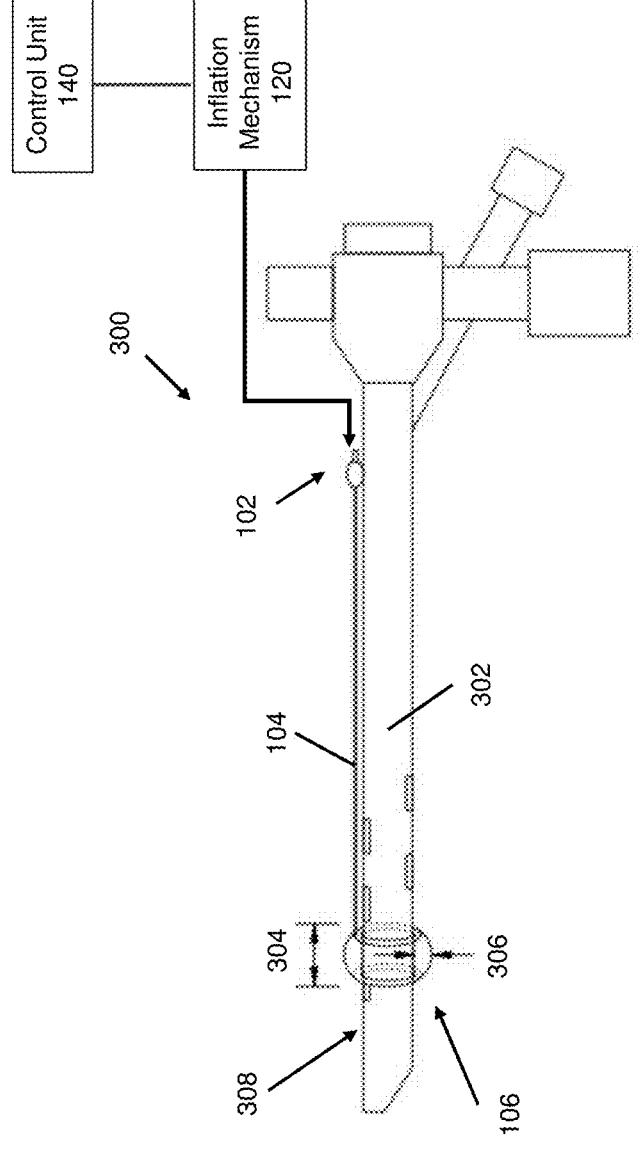
FIG. 3 illustrates the balloon device of FIG. 1 installed on a barrel of a rigid bronchoscope device.

FIG. 3 illustrates how the balloon device 100 sits on the rigid bronchoscope 300. In this example, the main balloon member 106 is disposed at the distal tip 308 of the barrel 302. The main balloon member 106 is configured to be moved or slid up and down the rigid barrel 302 with the operator pulling or pushing the body or balloon shaft 104. The proximal end of the balloon shaft 104 will be outside of the patient's mouth for balloon inflation and deflation, if needed.

Referring to FIG. 3, the main balloon member 106 is configured to be disposed on an outside of a main shaft or barrel 302 of a rigid bronchoscope 300. The inner side of the balloon member 106 is configured to fit snugly against the barrel 302 of the rigid bronchoscope 300. The term "snugly", as that term is used herein, is generally intended to mean a fit that provides a seal and limits the passage of fluid or air between the balloon member 106 and the barrel 302.

In one embodiment, an inflation device or mechanism 120 is operably connected to the balloon shaft member 104 and the balloon member 106. The inflation mechanism 120 is operably connected to the inflatable balloon 306 in this example and is configured to adjust the inflation level of the balloon 306. In one embodiment, the inflation mechanism 120 comprises a pump 120 and a valve system to regulate the flow of inflation fluid into and out of the balloon 306.

In one embodiment, a control unit 140 is operably connected to the inflation mechanism 120. The control unit 140 is configured to provide precise control over the inflation and deflation of the balloon 306. In one embodiment, the control unit 140 a manual control interface allowing for manual adjustment of the balloon inflation level.

Referring again to FIG. 2, in the inflated state, the diameter 202 of the main balloon member 106, is configured to fit within the range of a normal trachea, such as in the range of 14 mm to and including 18 mm. In the example of FIG. 2, the diameter 202 can be in the range of 12 mm to 15 mm. In the example of FIG. 3, the width 304 of the balloon member 106 in the inflated state is approximately 10 mm, while the distance 306 from the outer edge of the barrel 302 to the outer edge of the inflated balloon member 306 is in the range of approximately 3-6 mm.

Figure 4:
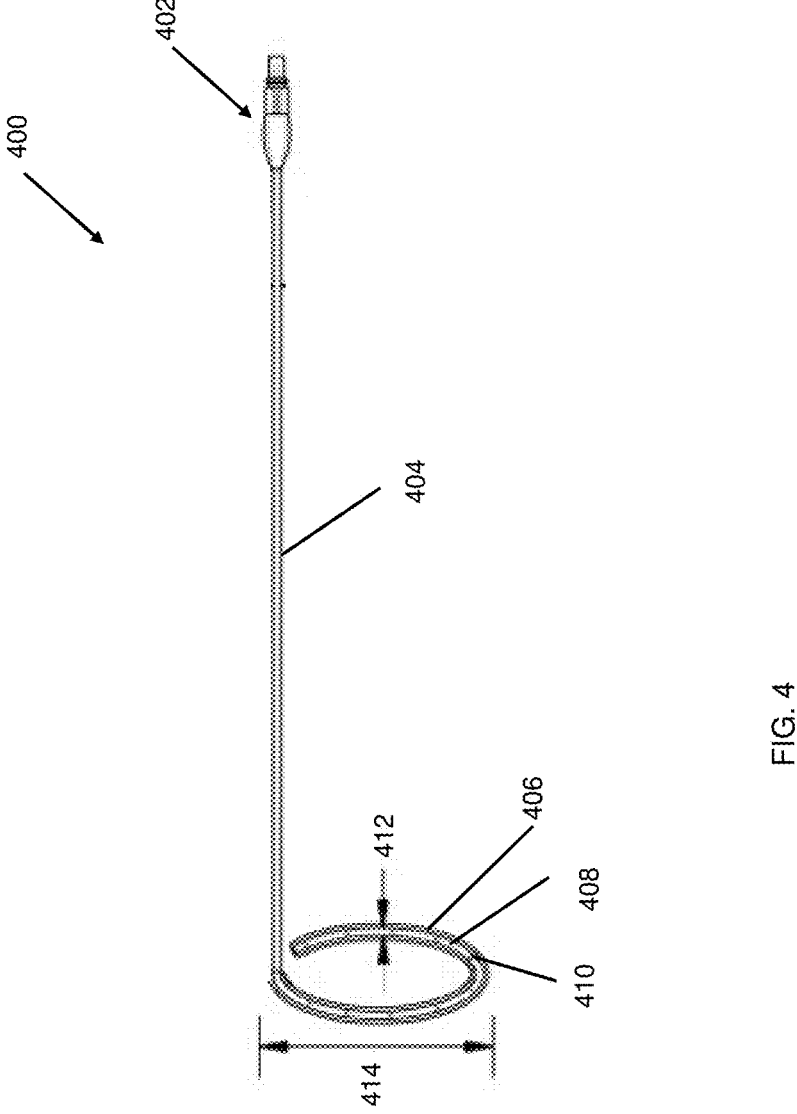
FIG. 4 illustrates a schematic block diagram of another embodiment of an exemplary ballon device for a rigid bronchoscope incorporating aspects of the present disclosure.

FIG. 4 illustrates another embodiment of a balloon device 400 for a rigid bronchoscope incorporating aspects of the disclosed embodiments. In the example of FIG. 4, the main balloon member 406 is fixated or disposed on or around a circular tube member 408. The circular tube member 408 is continuous with the balloon shaft or connecting tubing 404. The connecting tubing 404 is used to inflate the balloon member 406.

The circular tube member 408 is a plastic tube, which includes fenestrated holes or apertures 410. The fenestrated holes 408 are configured to allow the air to pass through in order to inflate the balloon member 402 when air is delivered via the connecting tubing 404. In one embodiment, the circular tube member 408 is made of polyethylene.

In this embodiment, while the balloon member 406 is inflatable, it is not stretchable, as in the example of FIG. 1. The diameter 410 of the balloon member 406 is generally fixed by the diameter of the circular tube member 408.

The example of FIG. 4 shows the balloon member 406 in a deflated state. In the deflated state, a diameter 412 of the balloon member 406 is approximately 1 mm. The outer diameter 414 is in the range of approximately 11-14 mm, similar to the example of FIG. 1.

Figure 5:
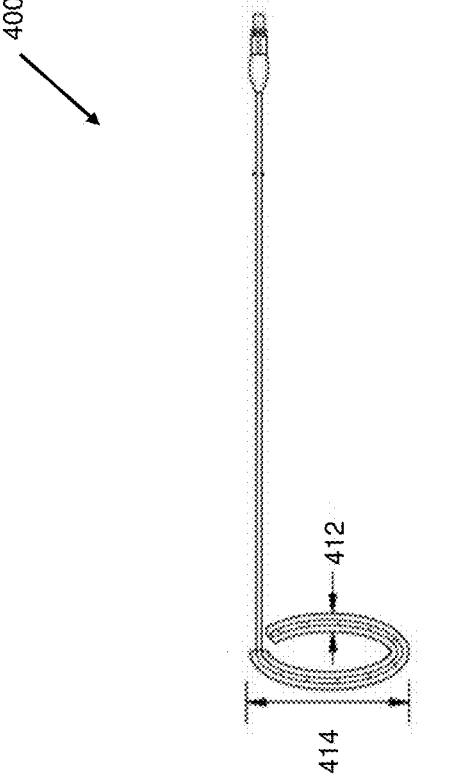
FIG. 5 illustrates the exemplary ballon device of FIG. 4 with the ballon inflated.

FIG. 5 illustrates the balloon member 406 in an inflated state. In the inflated state, the diameter 412 is in the range of 3 mm to and including 5 mm. The diameter 414 is in the range of 11 mm to 14 mm.

Figure 6:
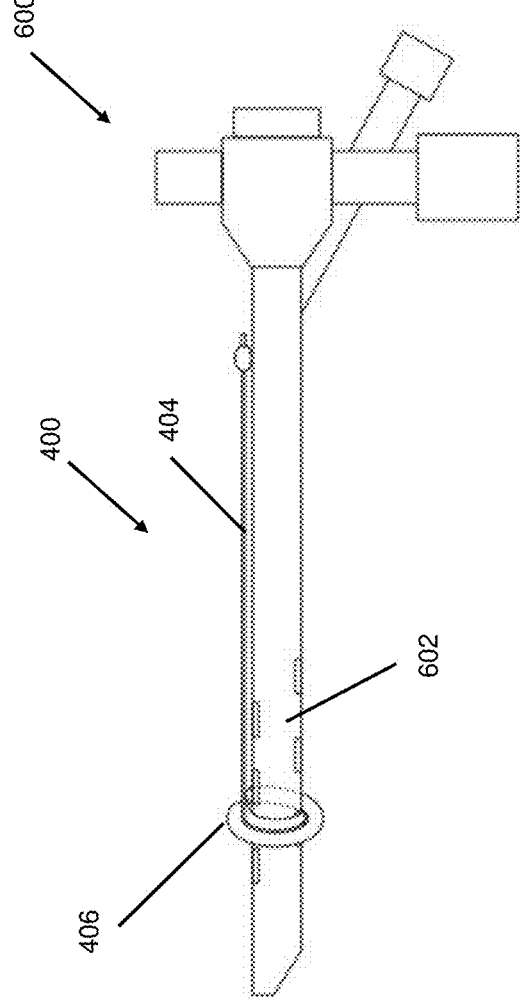
FIG. 6 illustrates the balloon device of FIG. 4 installed on a rigid bronchoscope device.

FIG. 6 illustrates the balloon device 400 disposed on a rigid bronchoscope 600. In one embodiment, the connecting tubing member 404, which is in the form of a shaft, can be used to move the balloon member 406 up and down the barrel 602 of the rigid bronchoscope 600.

Figure 7:
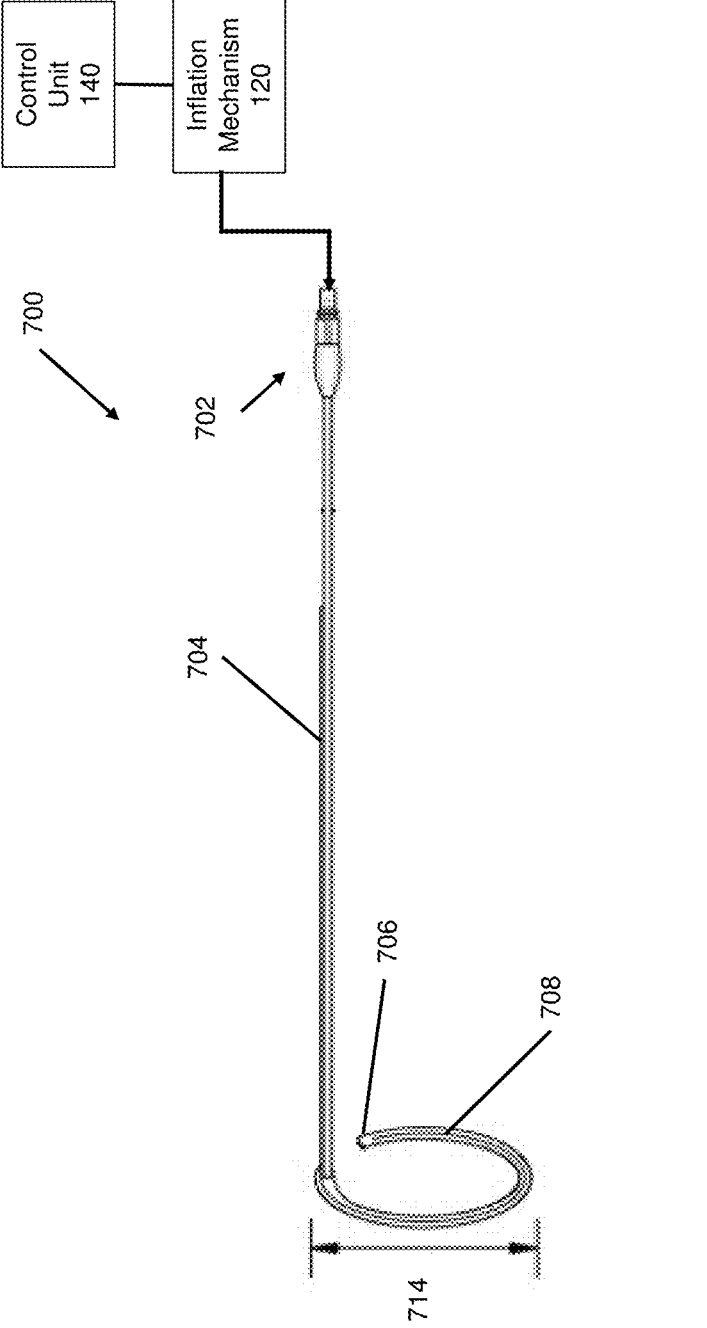
FIG. 7 illustrates a schematic block diagram of another embodiment of an exemplary ballon device for a rigid bronchoscope incorporating aspects of the present disclosure.
Figure 9:
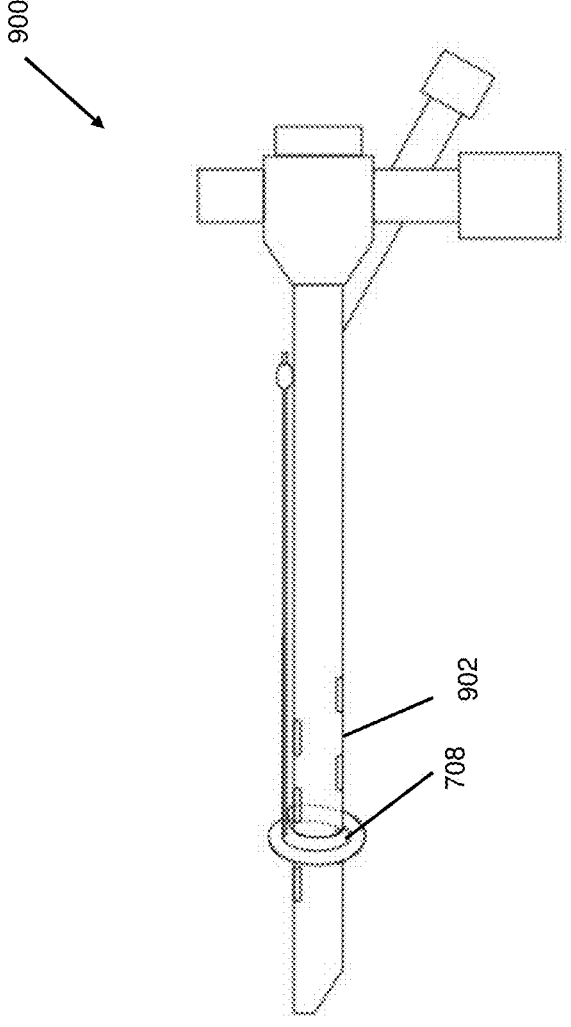
FIG. 9 illustrates the balloon device of FIG. 7 installed on a rigid bronchoscope device.

FIG. 7 illustrates another embodiment of a balloon device 700 for a rigid bronchoscope incorporating aspects of the disclosed embodiments. In this example, rather than the fenestrated circular tube member 408 as shown in FIG. 4, the core of the balloon member 706 is an adjustable metal strip 708. The adjustable metal strip 708 has an adjustable diameter and is configured to wrap around the shaft or barrel 902 of the rigid bronchoscope 900, as illustrated in FIG. 9.

In this example, the balloon member 706 is connected to or coupled along a perimeter of the adjustable metal strip 708. The balloon shaft or connecting tube 704 is connected to the balloon member 706 in this example, for inflation and deflation purposes. The adjustable metal strip 708 can also be attached to the balloon shaft 704 in a manner that allows the metal strip 708 to be adjusted around the barrel 902 of the rigid bronchoscope 900 by tightening and loosing. This secures the balloon member 706 to the shaft 704.

Figure 8:
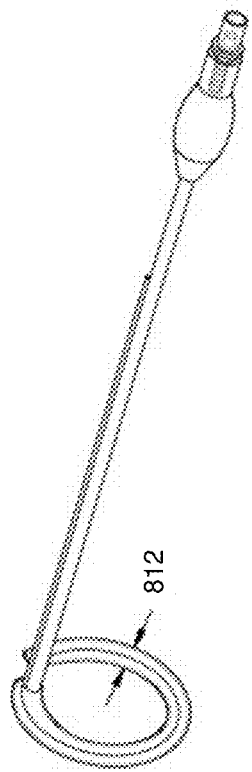
FIG. 8 illustrates the exemplary ballon device of FIG. 7 with the ballon inflated.

The diameter 714 in the example of FIG. 7 is in the range of to and including 11 mm to 14 mm. The dimension 812 of the inflated balloon member 708 shown in FIG. 8 is in the range of approximately 3 mm to and including 5 mm. The dimensions of the balloon device 700 are similar to the dimensions presented with respect to the previous embodiments.

The balloon device of the disclosed embodiments enables better ventilation of patient's undergoing rigid bronchoscopy and prevents back bleeding into the lung. An inflatable and adjustable balloon is configured to fit snugly on the outside of the rigid bronchoscope. Once the balloon is inflated, improved jet ventilation can occur with better resulting aeration.

FIG. 7 also illustrates an exemplary connection of an inflation device 120 to the balloon shaft member 704 and the balloon member 706. The inflation mechanism 120 is operably connected to the inflatable balloon 706 in this example and is configured to adjust the inflation level of the balloon 706. In one embodiment, the inflation mechanism 120 comprises a pump 120 and a valve system to regulate the flow of inflation fluid into and out of the balloon 706.

In one embodiment, a control unit 140 is operably connected to the inflation mechanism 120. The control unit 140 is configured to provide precise control over the inflation and deflation of the balloon 706. In one embodiment, the control unit 140 a manual control interface allowing for manual adjustment of the balloon inflation level.

Thus, while there have been shown, described, and pointed out, fundamental novel features of the invention as applied to the exemplary embodiments thereof, it will be understood that various omissions, substitutions and changes in the form and details of devices and methods illustrated, and in their operation, may be made by those skilled in the art without departing from the spirit and scope of the presently disclosed invention. Further, it is expressly intended that all combinations of those elements, which perform substantially the same function in substantially the same way to achieve the same results, are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A rigid bronchoscope assembly comprising:
a rigid bronchoscope including a barrel having an outer surface; and
a balloon device disposed on the outer surface of the barrel, the balloon device comprising:
a balloon shaft member comprising a hollow tube;
a balloon member connected to a first end of the balloon shaft member, the balloon member configured to fit over and extend circumferentially around the barrel of the rigid bronchoscope and, when inflated, to expand radially outward from the barrel to form a seal between the outer surface of the barrel and an airway wall;

an air installation port connected to a second end of the ballon shaft member away from the ballon member;
an inflation device comprising a pump and a valve, the inflation device connected to the air installation port, the inflation device configured to regulate a flow of inflation fluid into and out of the balloon member through the air installation port and adjust an inflation level of the balloon member in order to create the seal; and
a metal string member having an adjustable circular shape connected to an end of the balloon shaft member, the balloon member being connected to the metal string member, wherein a change of a diameter of the metal string member causes a corresponding change in a diameter of the ballon member around the outer surface of the barrel.

2. The balloon device of claim 1, wherein the balloon member comprises a biocompatible material.

3. A rigid bronchoscope comprising:
a rigid tubular barrel member configured for insertion into an airway of a patient, the barrel member having an outer surface and a distal tip;
an inflatable balloon member disposed circumferentially around the outer surface of the barrel member near the distal tip;
a balloon shaft member comprising a hollow tube connected to the balloon member and extending proximally along the barrel member;
an inflation device comprising a pump and a valve, the inflation device connected to the balloon shaft member and the balloon member and configured to regulate a flow of inflation fluid into and out of the balloon member to adjust an inflation level of the balloon member so as to form a seal between the barrel member and a wall of the airway;
a metal string member having an adjustable circular shape connected to an end of the balloon shaft member, the balloon member being connected to the metal string member, wherein an adjustment of a diameter of the metal string member causes a corresponding change in a diameter of the balloon member around the outer surface of the barrel; and
wherein the balloon shaft member is further configured to slidably move the balloon member along a length of the barrel member.

4. The rigid bronchoscope according to claim 3, wherein the balloon member is connected to the balloon shaft member so that movement of the balloon shaft member with respect to the barrel member causes corresponding movement of the balloon member over the outer surface of the barrel member.

5. The rigid bronchoscope according to claim 3, wherein the balloon member is disposed on an outer circumference of the rigid barrel member and is configured to expand radially outward from the rigid barrel member to create the seal.

6. The rigid bronchoscope according to claim 5, wherein the balloon member, when inflated to form the seal, prevents leakage of air and fluid between the rigid barrel member and the airway during bronchoscopy.

7. The rigid bronchoscope according to claim 3, wherein the balloon shaft member is configured to slidably move the balloon member along a length of the rigid barrel member between proximal and distal positions on the rigid barrel member.

* * * * *